(12) United States Patent
Delamarche et al.

(10) Patent No.: US 10,653,349 B2
(45) Date of Patent: May 19, 2020

(54) DIAGNOSTIC APPARATUS

(71) Applicant: INTERNATIONAL BUSINESS MACHINES CORPORATION, Armonk, NY (US)

(72) Inventors: Emmanuel Delamarche, Thalwil (CH); James L. Hedrick, Pleasanton, CA (US); Minhua Lu, Mohegan Lake, NY (US); Vince S. Siu, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 684 days.

(21) Appl. No.: 15/296,657

(22) Filed: Oct. 18, 2016

(65) Prior Publication Data

US 2018/0103884 A1   Apr. 19, 2018

(51) Int. Cl.
*A61B 5/15*       (2006.01)
*H04W 4/20*      (2018.01)
(Continued)

(52) U.S. Cl.
CPC ...... *A61B 5/150854* (2013.01); *A61B 5/0022* (2013.01); *A61B 5/145* (2013.01); *A61B 5/157* (2013.01); *A61B 5/150022* (2013.01); *A61B 5/150221* (2013.01); *A61B 5/150229* (2013.01); *A61B 5/150358* (2013.01);
(Continued)

(58) Field of Classification Search
CPC ............ A61B 5/150854; A61B 5/4851; A61B 5/150358; A61B 5/150984; A61B 5/0022; A61B 5/150755; A61B 5/150221; A61B 5/150229; A61B 5/1455; A61B 5/1486;
(Continued)

(56) References Cited

U.S. PATENT DOCUMENTS 6,540,675 B2 *  4/2003  Aceti ................ A61B 5/14532
                                                                600/309
6,887,202 B2 *  5/2005  Currie ............... A61B 5/14532
                                                                600/309
(Continued)

OTHER PUBLICATIONS

Wei Wang et al., High-Pressure Open-Channel On-Chip Electroosmotic Pump for Nanoflow High Performance Liquid Chromatography, Anal. Chem. 2014, 86, pp. 1958-1964, Jan. 21, 2014.

*Primary Examiner* — Eric F Winakur
(74) *Attorney, Agent, or Firm* — L. Jeffrey Kelly; Otterstedt, Wallace & Kammer, LLP

(57) ABSTRACT

A diagnostic patch apparatus has a sampling module that includes sampling means for sampling fluid from a patient's skin when the sampling module is placed against the patient's skin, and a sample chamber coupled in fluid communication with the sampling means. The apparatus also has an analysis module that includes a fluid conduit coupled in fluid communication with the sample chamber of the sampling module and a plurality of sensors coupled in fluid communication with the fluid conduit. The apparatus also may have a reader module that includes at least one optical sensor coupled in optical communication with the analysis module, a microcontroller coupled in electrical communication with the at least one sensor of the analysis module, and a wireless communication package coupled in electrical communication with the microcontroller.

14 Claims, 7 Drawing Sheets

(51) Int. Cl.
| | |
|---|---|
| *H04L 29/08* | (2006.01) |
| *A61B 5/00* | (2006.01) |
| *A61B 5/1455* | (2006.01) |
| *A61B 5/1486* | (2006.01) |
| *A61B 5/02* | (2006.01) |
| *A61B 5/157* | (2006.01) |
| *A61B 5/145* | (2006.01) |

(52) U.S. Cl.
CPC ...... *A61B 5/150984* (2013.01); *A61B 5/4851* (2013.01); *A61B 5/6833* (2013.01); *H04L 67/104* (2013.01); *A61B 5/02035* (2013.01); *A61B 5/1486* (2013.01); *A61B 5/14532* (2013.01); *A61B 5/14539* (2013.01); *A61B 5/14546* (2013.01); *A61B 5/14551* (2013.01); *A61B 5/150755* (2013.01); *A61B 5/4585* (2013.01); *A61B 5/685* (2013.01); *A61B 2560/0412* (2013.01)

(58) Field of Classification Search
CPC ..... A61B 5/6833; A61B 5/157; A61B 5/7264; A61B 5/746; A61B 5/7282
See application file for complete search history.

(56) References Cited

U.S. PATENT DOCUMENTS

| | | | |
|---|---|---|---|
| 8,037,903 | B2 | 10/2011 | Wang et al. |
| 9,033,898 | B2 | 5/2015 | Chickering, III et al. |
| 9,119,578 | B2 | 9/2015 | Haghgooie et al. |
| 2004/0096959 | A1* | 5/2004 | Stiene ................ A61B 5/1473 435/287.2 |
| 2010/0269837 | A1 | 10/2010 | Levinson et al. |
| 2011/0172508 | A1 | 7/2011 | Chickering, III et al. |
| 2011/0172510 | A1 | 7/2011 | Chickering, III et al. |
| 2013/0211289 | A1 | 8/2013 | Moga et al. |
| 2014/0038306 | A1 | 2/2014 | Berthier et al. |
| 2017/0055890 | A1* | 3/2017 | Kube ................ A61B 5/14532 |

* cited by examiner

DIAGNOSTIC APPARATUS

BACKGROUND

The present invention relates to the medical arts, and, more particularly, to monitoring and diagnosis of infections and the like.

Total joint replacement is a surgical procedure to remedy skeletal or cartilaginous injuries that severely limit daily life. Joint replacement surgeries are relatively common.

Bacterial infection of the synovial cavity is a relatively uncommon but dangerous post-surgical complication of total joint replacement. Such infections are difficult to effectively treat because blood does not typically permeate the synovial cavity, which makes it difficult to deliver antibiotics to kill the unwelcome bacteria. Accordingly, early stage detection of synovial infections can improve a patient's outcome, when antibiotics can be orally or intravenously administered while the bacteria count is low. Currently, synovial infections are diagnosed by aspirating the synovial cavity using a syringe. The aspirated fluid then is sent out to a laboratory for analysis.

Various medical conditions, such as infections, chronic diseases, or acute illnesses, produce biomarkers that permeate a person's blood and interstitial fluid. For example, biomarkers may include (by way of non-limiting examples) temperature; sugars such as glucose; ions such as sodium, potassium, chloride, calcium, magnesium, bicarbonate, and/or hydronium (pH); gases such as carbon dioxide, oxygen, nitrogen, or carbon monoxide; metabolites such as urea, creatinine, taurine, or acetaldehyde; proteins such as IL-6 (Interleukin 6), C-reactive protein or clotting factors; and cell count from white blood cells and erythrocytes.

Blood and interstitial fluid can be sampled by minimally invasive techniques, for example, using microneedles to penetrate into or beneath the skin without puncturing venous or muscular tissue. Sampled fluid can be analyzed onboard a sampling device, and simple diagnoses (e.g., an indication of high biomarker level or a direction to take a dose of medication) can be generated by the sampling device based on the analysis of the sampled fluid.

SUMMARY

According to an embodiment of the present invention, a method for monitoring bone implant health includes the step of applying a diagnostic apparatus to skin adjacent a knee joint in order to assess for the presence of synovial cavity infection surrounding a knee implant.

Accordingly, aspects of the invention provide a diagnostic patch apparatus, which includes a sampling module, an analysis module, and a reader module. The sampling module includes a sampling means for sampling fluid from a patient's skin when the sampling module is placed against the skin; and a sample chamber that is coupled in fluid communication with the sampling means. The analysis module includes a fluid conduit that is coupled in fluid communication with the sample chamber of the sampling module; and a plurality of sensors that are coupled in fluid communication with the fluid conduit. The reader module includes a microcontroller that is coupled in electrical communication with the plurality of sensors of the analysis module; and a wireless communication package that is coupled in electrical communication with the microcontroller.

Other aspects of the invention provide a diagnostic patch apparatus, which includes a sampling module and an analysis module. The sampling module includes at least one sampling microneedle that is positioned to penetrate a patient's skin when the sampling module is placed against the skin; and a sample chamber that is coupled in fluid communication with the sampling microneedle. The analysis module includes a fluid conduit that is coupled in fluid communication with the sample chamber of the sampling module; and a plurality of sensors that are coupled in fluid communication with the fluid conduit.

Other aspects of the invention provide a system, which includes a sampling module, an analysis module, a reader module, and a cloud-computing node. The sampling module includes sampling means for sampling fluid from a patient's skin when the sampling module is placed against the skin; and a sample chamber coupled in fluid communication with the sampling means. The analysis module includes a fluid conduit coupled in fluid communication with the sample chamber of the sampling module; and at least one sensor coupled in fluid communication with the fluid conduit. The reader module includes a microcontroller coupled in electrical communication with the at least one sensor of the analysis module; and a wireless communication package coupled in electrical communication with the microcontroller. The cloud computing node is coupled in wireless communication with the wireless communication package of the reader module and is configured to transfer reader module data to a cloud environment.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide one or more of the following advantages:

Minimally invasive diagnosis of disease, infection, or illness based on biomarkers in sample fluid, without the delay associated with conventional laboratory analysis.

Diagnosis of synovial cavity infections without the invasive procedure of syringe aspiration of the cavity.

Microfluidic aspect of the invention means small amounts of fluid and reagents are required for diagnosis compared to traditional volumes drawn from synovial fluid aspirations.

According to embodiments of the invention, multiple onboard sensors, for multiplex panel of biomarkers, improve the sensitivity and specificity of clinical diagnosis.

Embodiments of the invention can be applied soon after surgery to monitor for onset of infection, rather than waiting for gross symptoms of infection to present.

If infection is present, proposed device can determine if the infection is caused by gram-positive or gram-negative bacteria by probing for cell surface markers or accessory proteins secreted by these respective organisms. Speciation is key to guiding the administration of proper and effective antibiotic treatment.

Embodiments of the invention can be used for post-treatment monitoring to detect recurrence of a treated infection. Rather than requiring hospitalization or outpatient visits for repeated synovial aspiration, patient status can be monitored at home via the cloud connection of the inventive apparatus.

These and other features and advantages of the present invention will become apparent from the following detailed description of illustrative embodiments thereof, which is to be read in connection with the accompanying drawings.

DETAILED DESCRIPTION

Figure 1:
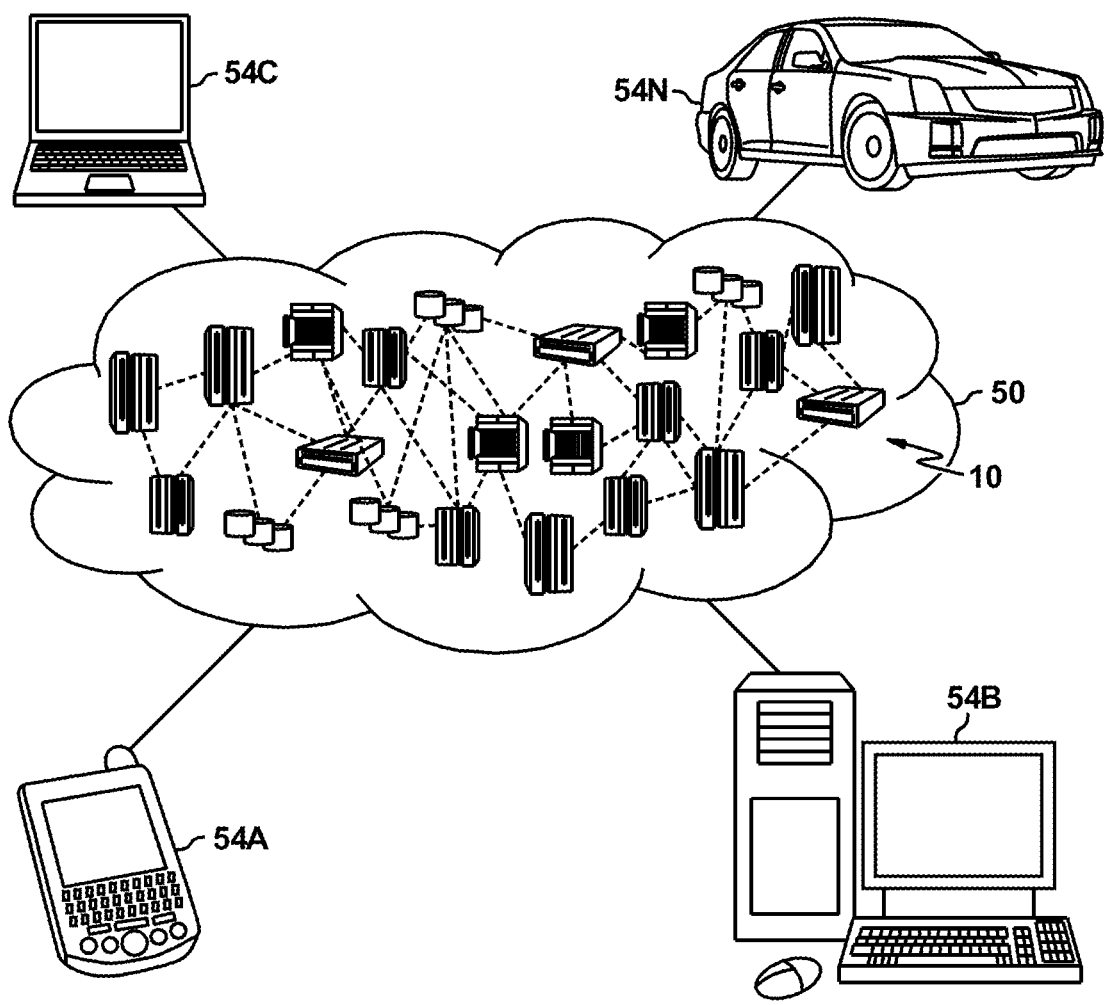
FIG. 1 depicts a cloud computing environment according to an embodiment of the present invention.

The subject matter of the instant application will be described with reference to illustrative embodiments. Numerous modifications can be made to these embodiments and the results will still come within the scope of the invention. No limitations with respect to the specific embodiments described herein are intended or should be inferred.

Although a particular embodiment of the invention is described in detail herein with reference to detecting infections in knee joints, it is to be understood that the invention is equally applicable to other diagnostic purposes, e.g., hydration monitoring, blood glucose and lactate monitoring, or cancer screening.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
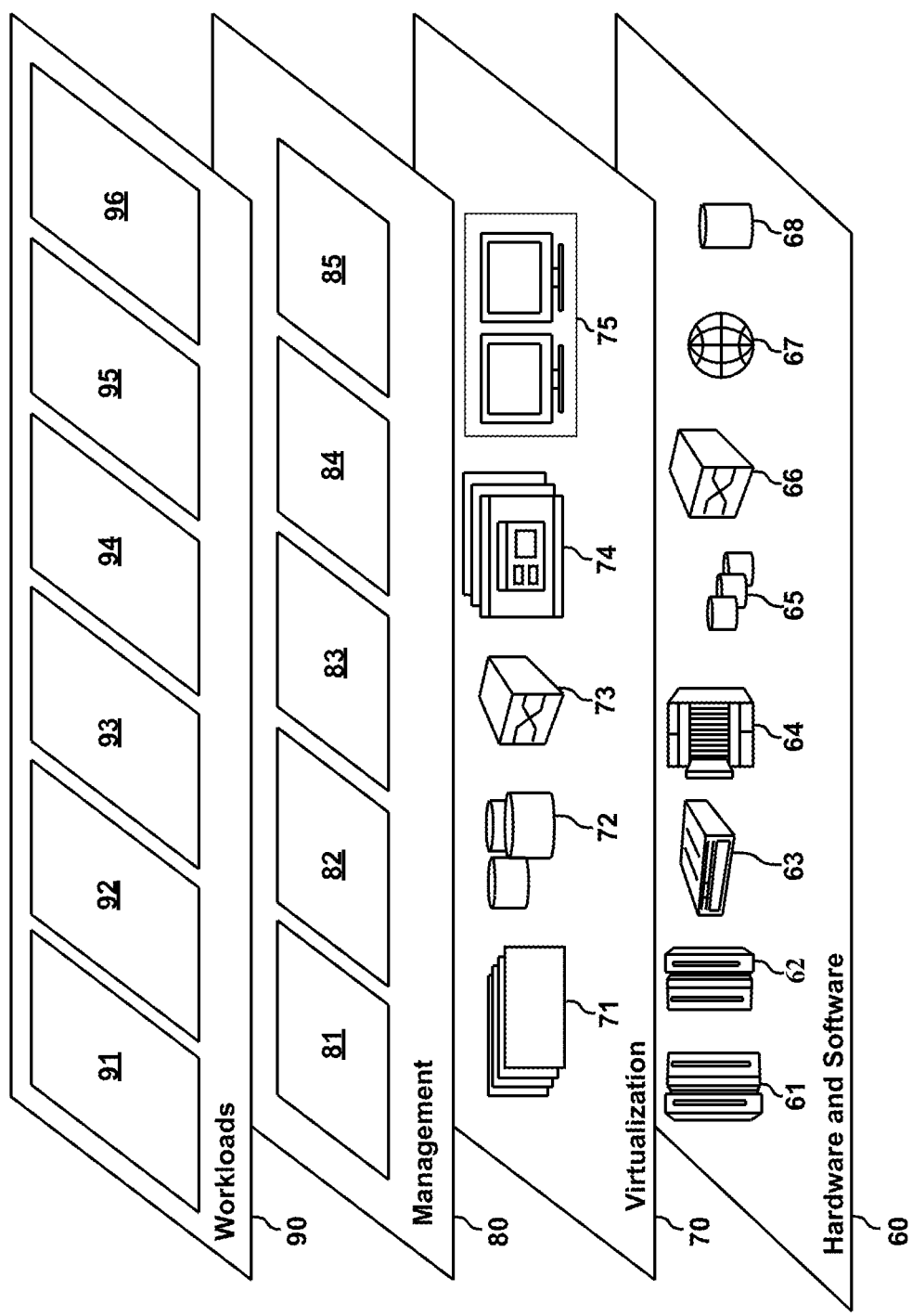
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and sample fluid diagnostics 96.

Figure 3:
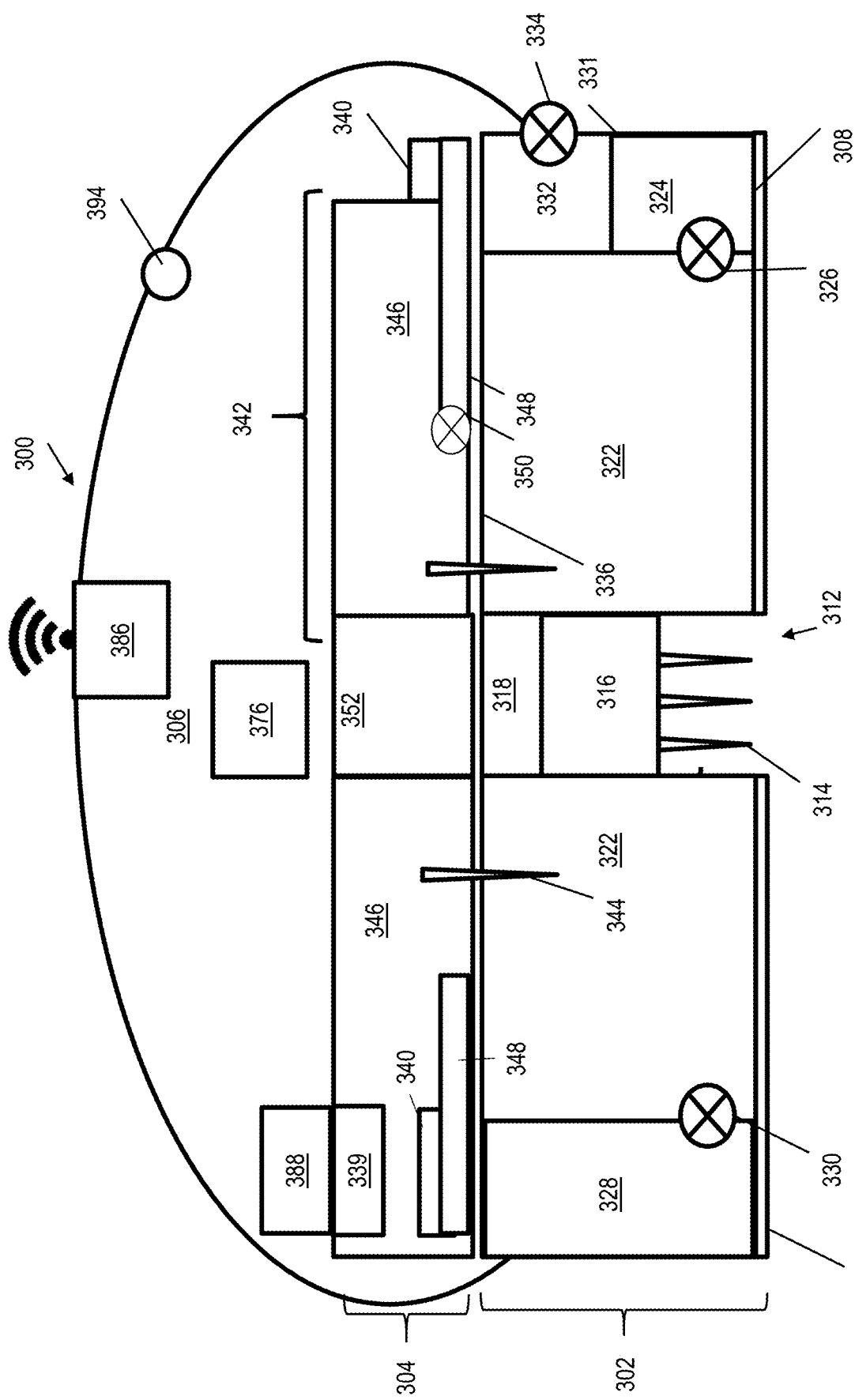
FIG. 3 shows a diagnostic apparatus according to embodiments of the invention.

Referring to FIG. 3, a diagnostic patch 300 includes a sampling module 302, an analytic module 304, and a reader module 306. The sampling module 302 collects a sample fluid from or through a patient's skin. The analysis module 304 measures properties of the sample fluid. The reader module 306 obtains measurements from the analysis module 304 and facilitates processing of the measurements to assess a patient's diagnostic status; the reader module 306 also provides power (e.g., electrical and/or mechanical power) to the sampling module 302 and to the analysis module 304, in embodiments in which those modules have powered components.

Figure 4:
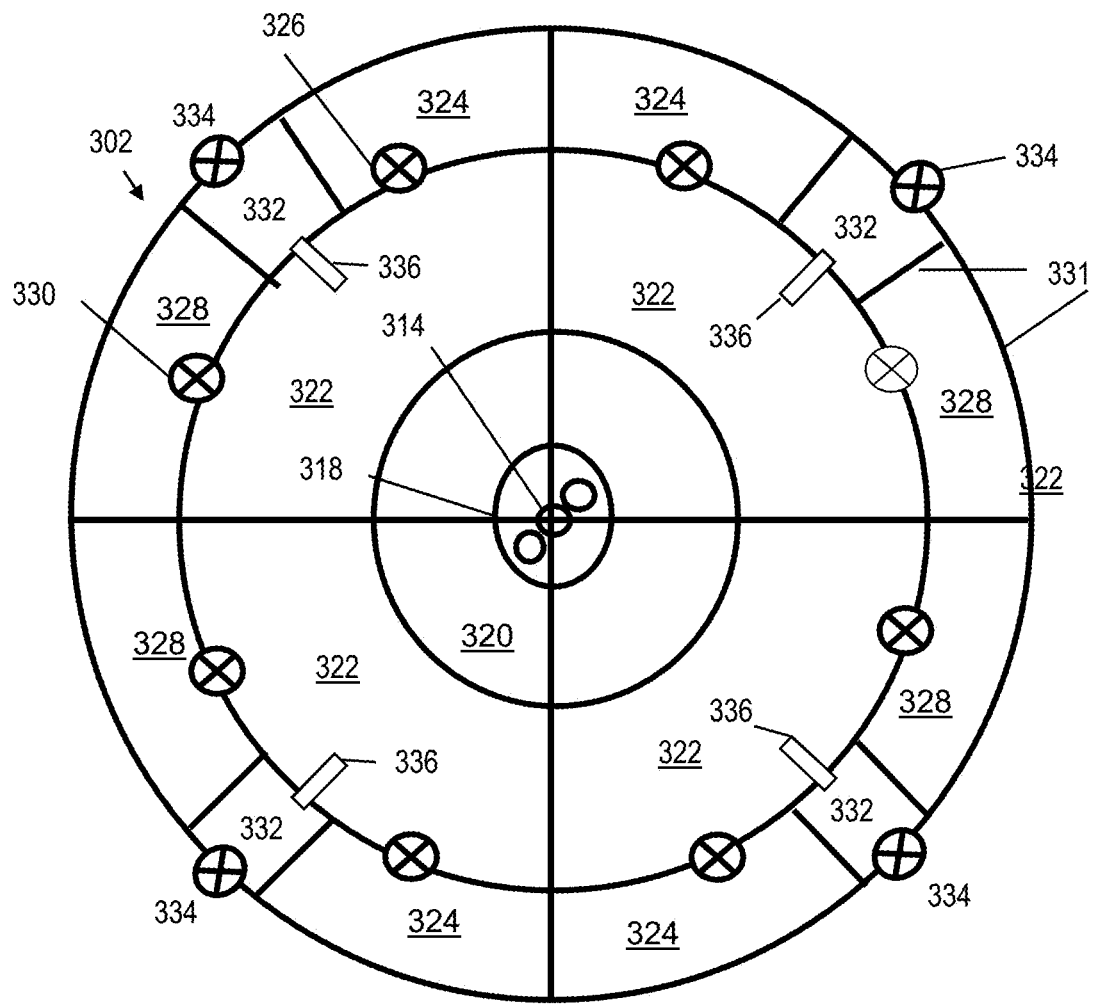
FIG. 4 shows a sampling module of the apparatus of FIG. 3.

Referring now to FIGS. 3 and 4, the sampling module 302 includes a base 308, which has an optional adhesive layer 310 surrounding an opening 312. In certain embodiments, the sampling module 302 includes one or more microneedle(s) 314 that are housed in the opening 312, along with an actuator 316 for microneedle insertion into the patient's skin. In other embodiments, the microneedle(s) 314 are mounted integrally onto the base 308 so that the microneedles are inserted by pressing the base against the patient's skin. In at least one embodiment, the microneedle(s) 314 are positioned on the sampling module 302 so that they penetrate a patient's skin when the sampling module is placed against the skin.

Figure 5:
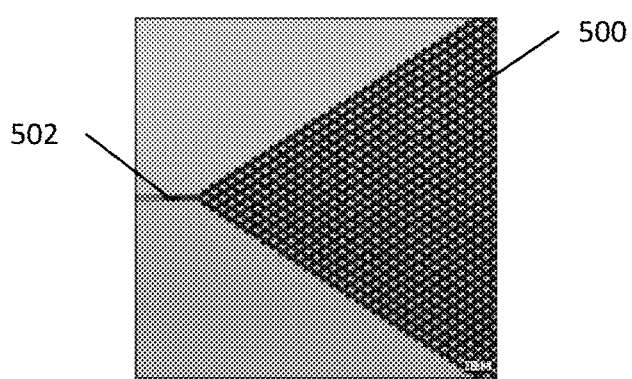
FIG. 5 shows a capillary pump usable in the sampling module of FIG. 4.

According to an embodiment of the present invention, the sampling module 302 includes a sample pump 318 for extraction of sample fluid through the microneedles. In certain embodiments, the sample pump 318 assists in forcing the sample fluid (e.g., blood or interstitial fluid) through a filter 320 that is disposed between the microneedle 314 and a sample chamber 322. According to an embodiment of the present invention, the filter 320 is, for example, a blood cell filter that separates red and/or white blood cells from the sample fluid. Possible filtration methods include filter paper, sponge, pillar-based or trough-based microfilters. The filter is optional if cells, and in particular red blood cells, do not interfere with the analysis and mechanism used for generating a signal in the analysis module 304. If only ionic conductivity or turbidity of the sample is measured, using a filter may be omitted. On the other hand, in case the analysis module 304 is meant to generate a light-based or electrochemical-based signal, then it is preferable to filter cells. In principle, capillary forces can be sufficient to have the liquid pass the blood filter and proceed to an analysis chamber. However, if large volumes of sample need to be passed through the filter and the analysis chamber, an active pumping mechanism might be preferred. Such an active pumping mechanism can also displace a relatively large (several microliters) volume of sample, which might be need if analytes need to be detected with high-sensitivity. Thus, in at least one embodiment, the sample pump 318 is, for example, a vacuum pump; a piston pump; or a solid state pump such as a capillary pump (an example is shown in FIG. 5, wherein multiple pumping microchannels 500 provide enhanced capillary action to suction fluid through an input microchannel 502) or an electroosmotic pump. The sample chamber 322, which is coupled in fluid communication with the microneedle 314, stores the sample fluid after it is obtained from a patient through the microneedle 314.

According to an embodiment of the present invention, adjacent to the sample chamber 322, the sampling module 302 includes a reagent chamber 324 that is coupled in fluid communication with the sample chamber for storing and supplying reagent into the sample chamber to prevent coagulation of the sample fluid (in case the sample fluid is, e.g., blood). Suitable anticoagulant reagents are known to those having ordinary skill in the art. In certain embodiments, the reagent chamber 324 are coupled to the sample chamber 322 via a reagent valve 326. According to an embodiment of the present invention, the reagent valve 326 is, by way of example without limitation, a diaphragm valve; a pinch valve; an electrostatic valve; an electrolytic bubble valve; or a hydrophobic timing valve. A hydrophobic timing valve is one in which the surface of a microchannel, which is initially hydrophobic, gradually becomes wetted by the sample fluid. As the microchannel becomes wetted, for example due to pressure from the sample pump 318, then fluid begins to diffuse in both directions along the microchannel. In at least one exemplary embodiment of the present invention, a hydrophobic timing valve that couples the reagent chamber 324 to the sample chamber 322 permits admission of reagent into the sample chamber after a predetermined amount of sample fluid has filled the sample chamber based on design flowrate through the sample pump 318.

According to an embodiment of the present invention, also adjacent to the sample chamber 322, the sampling module 302 includes a diluent chamber 328 that is coupled in fluid communication with the sample chamber to store and supply diluent to the sample fluid to prepare the sample for analysis in the analysis module 304. In certain embodiments, the diluent chamber 328 is coupled to the sample chamber 322 via a diluent valve 330. As discussed above with reference to the reagent valve 326, the diluent valve 330 can be modified to have a different design, and embodiments described herein are not intended to be limiting.

In certain embodiments, the sampling module 302 includes an array of multiple sample chambers 322 with corresponding reagent chambers 324 and diluent chambers 328. Each of the sample chambers 322 can be actuated separately for different diluent and reagent if needed. In embodiments for which only one type of diluent and reagent are required and the reagent does not degrade the diluent, the reagent and diluent can be pre-loaded into the sample chamber. Once the reagent and the diluent are in the sample chamber 322 with the sample fluid, various mixing mechanisms are acceptable (e.g., vibration, convective heating, stirring).

The various chambers of the sampling module 302 are defined by walls, e.g., 331, which in certain embodiments are flexible to conform to a patient's skin surface. For example, the walls 331 are constructed of a flexible biocompatible material such as PET PDMS, NAFION, etc.

The sampling module 302 also may include a sponge or overflow volume 332 and/or a leak valve 334 to mitigate potential sample overflow, as well as a metering structure 336 for gauging and controlling sample volume. As an example of the metering structure 336, differential flow resistance can be used: The mechanism 336 can be a junction having a wider and a narrower microchannel. The wider microchannel should be in communication with the sample chamber 322 and the narrower microchannel should be in communication with the "sponge" or sample overflow volume 332. The sample will pass preferentially through the wider microchannel because this flow path will have a lower fluidic resistance. Once the sample chamber 322 will be filled, the flow will only proceed through the sample overflow volume 332 via the narrower junction. Since flow rate is directly inversely proportional to the hydraulic resistance of a conduit, the dimensions of the microchannels forming the junction will define how much liquid will pass to the sample chamber 322 and overflow volume 332. In a preferred example, approx. 75% of the sample should pass directly to the sample chamber 322 and approx. 25% of the sample should pass in parallel to the overflow volume 332. Once the sample chamber 322 is filled, all the excess sample will pass to the overflow volume 332.

As mentioned above, in at least one embodiment of the present invention, the sampling module 302 includes powered components (for example, the sample pump 318 and/or the valves 326, 330). In such a case, the sampling module 302 also includes electrical leads to connect to the reader module 306 or to the analysis module 304 (in case electrical power is delivered via the analysis module rather than directly from the reader module). In certain embodiments, in which the sample pump 318 and/or the valves 326, 330 are electrically powered, the sampling module 302 includes a microcontroller chip (not shown) for controlling sample collection and preparation. In other embodiments, the microcontroller is integrated into the reader module 306 as a microprocessor 376, further discussed below.

Figure 6:
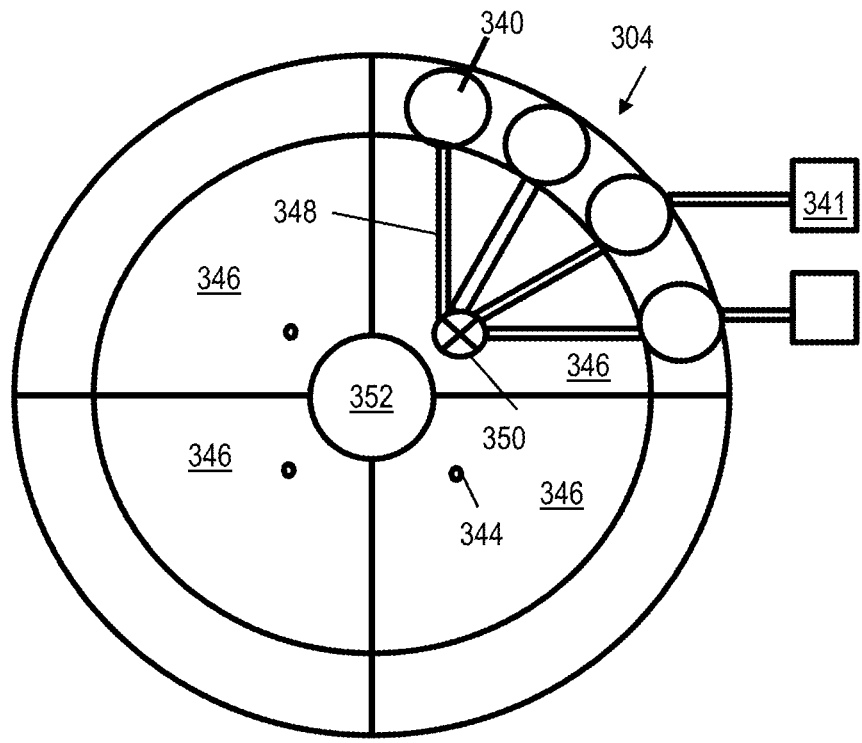
FIG. 6 depicts an analysis module of the apparatus of FIG. 3.

Referring now to FIGS. 3 and 6, in some embodiments the analysis module 304 is mounted at a second surface of the sampling module 302, opposite the first surface from which the microneedles 314 protrude. According to an exemplary embodiment of the present invention, the analysis module 304 is mounted to the sampling module 302 by piercing insertion of microneedles 344 into the sample chamber(s) 322. Additionally or alternatively, the analysis module 304 is mounted to the sampling module 302 by interference fit of a rim of the analysis module around the walls 331 of the sampling module. In at least one embodiment where the analysis module 304 is mounted at the second surface of the sampling module 302, the analysis module 304 includes at least one window 339. According to an exemplary embodiment of the present invention, the window 339 is formed of a translucent or transparent material suitable for optical (e.g., visible, near-infrared, or infrared) transmission and fluid containment. Alternatively, the window 339 is an opening surrounded by a containment wall. The purpose and function of the window 339 will be further discussed below with reference to the reader module 306.

The analysis module includes at least one sensor 340. Each sensor 340 has a corresponding electrical lead 341 for connection with the reader module 306. Each sensor 340 is connected in fluid communication with the sample chamber 322 of the sampling module 302 via an associated fluid conduit 342. In certain embodiments, multiple sensors 340 have corresponding individual fluid conduits 342. In certain embodiments, each fluid conduit 342 includes at least one microneedle 344, which punctures the sample chamber 322 of the sampling module 302. Each fluid conduit 342 also may include a sample sub-chamber 346; on the other hand, multiple fluid conduits may share a single sample sub-chamber 346 that is connected in fluid communication with the microneedle 344. Each fluid conduit 342 includes a microchannel 348 that connects the sample sub-chamber 346 to the at least one sensor 340, and may include a sensor valve 350 that controls flow through the microchannel to the at least one sensor. As discussed above with reference to the other valves 326, 330, various types of valves are suitable for controlling flow from the microchannel 348. Although the sensor valve 350 is shown disposed in the sample sub-chamber 346 at the "head" of the microchannels 348, in other embodiments the sensor valve(s) 350 is disposed in downstream portions of the microchannels. The analysis module 304 also may include an analyte pump 352 that draws vacuum on the sample sub-chamber 346 in order to induce flow through the microneedle(s) 344 from the sample chamber 322. Appropriate pump designs will be apparent to those of ordinary skill in the art.

Figure 7:
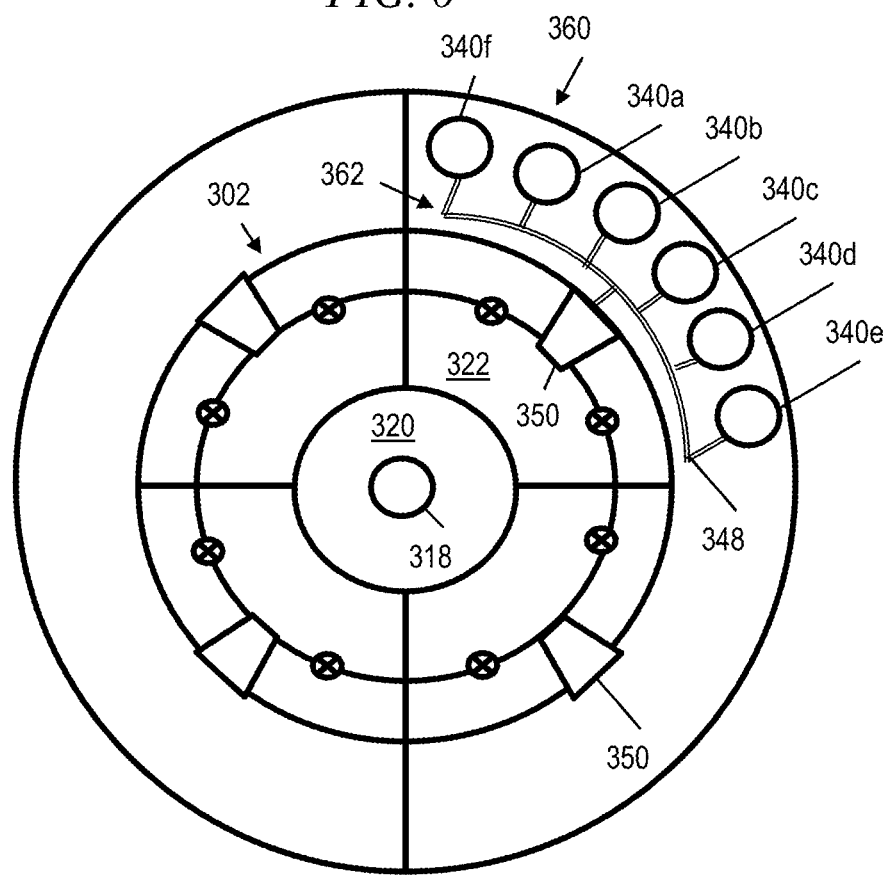
FIG. 7 depicts a sampling module and an analysis module, according to an alternative embodiment of the invention.

In other embodiments, as shown for example in FIG. 7, an analysis module 360 is mounted surrounding the sampling module 302. In FIG. 7, components similar to those of FIGS. 3 and 6 are similarly numbered and are not discussed in detail. Again, the analysis module 360 includes at least one sensor 340, which is connected in fluid communication with the sample chamber 322 of the sampling module 302 via a fluid conduit 362. In these embodiments, the fluid conduit 362 includes a microchannel 348 and a sensor valve 350. According to an exemplary embodiment of the present invention, the microchannel 348 is multiply branched, as shown in FIG. 7, so that the single sensor valve 350 controls flow from the sample chamber 322 to all of the sensors 340. Alternatively, each sensor 340 has its own corresponding fluid conduit 362 to connect with the sample chamber 322. Although the sensor valve 350 is shown disposed at the wall 331 of the sample chamber 322, in at least one embodiment the microchannel 348 penetrates the wall 331, and the sensor valve(s) 350 are disposed downstream between the wall 331 and the sensor(s) 340.

The sensors 340 are configured to sense one or more of various analytes. According to an exemplary embodiment of the present invention, the sensors 340 are configured to detect the presence and/or concentration of one or more biomarkers including temperature; sugars such as glucose; ions such as sodium, potassium, chloride, calcium, magnesium, bicarbonate, and/or hydronium (pH); gases such as carbon dioxide, oxygen, nitrogen, or carbon monoxide; metabolites such as urea, creatinine, taurine, or acetaldehyde; proteins such as IL-6, C-reactive protein or clotting factors; and cell count from white blood cells and erythrocytes. Such sensors may include, for example, ion selective electrode(s); impedance sensor(s); viscosity sensor(s); photocell(s); pH electrode(s) or temperature sensor(s) for assessing turbidity or color of sample fluid.

Figure 8:
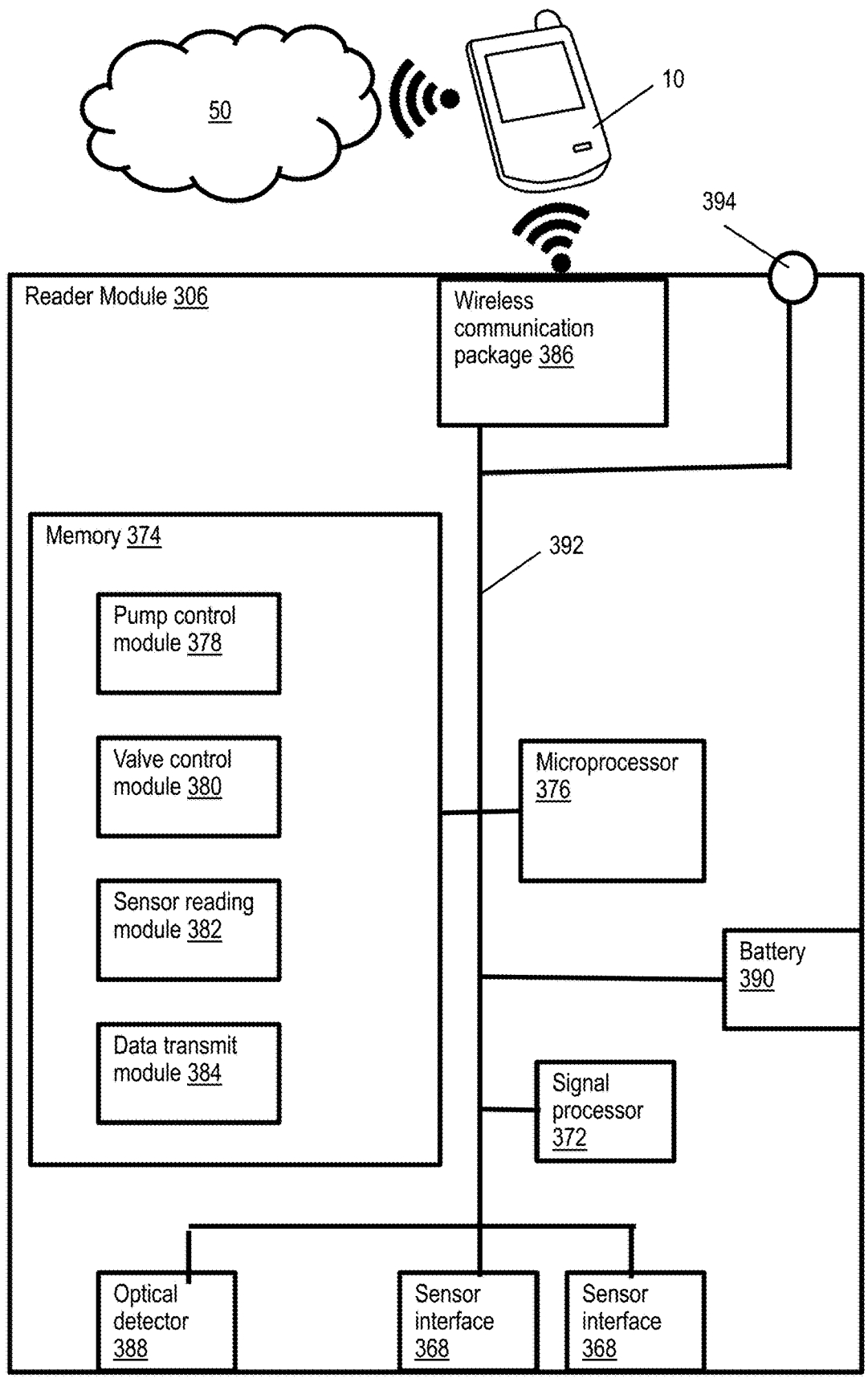
FIG. 8 shows in schematic view a reader module of the apparatus of FIG. 3, interacting with the cloud computing node and cloud computing environment of FIGS. 1-2.

Referring now to FIGS. 3 and 8, the reader module 306 includes one or more sensor interfaces 368, which connect with the electrical leads 341 of the analysis module 304 to provide electrical power to the various sensors 340 and to read the sensor outputs. The reader module 306 also includes one or more signal processors 372, a memory 374, a microprocessor 376, a wireless communication package 386, and an optical detector 388. The reader module 306 is powered by a battery 390, which also powers the analysis module 304 and the sampling module 302. According to an exemplary embodiment of the present invention, the battery 390 is recharged by energy harvesting, wirelessly, or by plugging into a conventional power source.

According to an exemplary embodiment of the present invention, the signal processor(s) 372 are dedicated each to a single signal interface 368, or are multiplexed so that a single signal processor serves several or all of the sensor interface(s) 368. The signal processor(s) generally accomplish filtering and amplification of sensor outputs detected by the sensor interface(s) 368, and convert the filtered and amplified signals to digital data suitable for storage and processing by the memory 374 and the microprocessor 376.

The memory 374 stores sensor data obtained from the signal processor(s) 372 as well as a database of values that are used for local analytics of the sensor data. Local analytics accomplished by the reader module include monitoring and comparing the real-time values of measured analytes to a stored average and/or preset threshold values and indicates values as normal or at risk. If threshold values are exceeded, reader will trigger an alert to inform patient or caretaker. The memory 374 also stores software modules that are executable by the microprocessor 376. The software modules include, for example, an actuation and pump control module 378; a valve control module 380; a sensor reading module 382; and a data transmit module 384. In certain embodiments, one or more of these modules may be omitted according to whether the compatible components are present in the sampling module 302 and/or the analysis module 304.

The microprocessor 376 is connected in electrical communication with the other components of the reader module 306, and with the powered components of the sampling module 302 and the analysis module 304. In particular, the microprocessor 376 is coupled in electrical communication with the sensors 340 via the aforementioned sensor interface(s) 368 and signal processor(s) 372. The microprocessor 376 is configured by the software modules stored in the memory 374 to control sample fluid acquisition, treatment by mixing the reagent and diluent, and transfer from the sampling module into the analysis module. More particularly, the microprocessor 376 is configured by the pump control module 378 to actuate at least one of the sample pump 318 or the analyte pump 352 in response to the microneedles 314 being inserted through a patient's skin. The microprocessor 376 is configured by the valve control module 380 to actuate the diluent valve 326, the reagent valve 330, and the sensor valve 350 to regulate flow of the sample fluid from the microneedles 314 to the sensors 340. The microprocessor 376 is configured by the sensor reading module 382 to energize the sensors 340 and to read the sensor results via the signal processor(s) 372. The microprocessor 376 also is configured by the data transmit module 384 to send data via the wireless communications package 386 to a cloud computing node 10, for example, a handheld wireless device such as a smart phone. Interactions of the cloud computing node 10 with the reader module 306 will be further discussed below.

In certain embodiments, in which the analysis module 304 is sandwiched between the sampling module 302 and the reader module 306, the optical detector 388 is disposed in registry with the window 339 of the analysis module 304. This arrangement registers the optical detector 388 in optical communication with the sample chamber 322 of the sampling module 302.

All of the electronic components of the reader module 306 are connected in communication with each other via a system bus 392.

Embodiments of the invention can be used for a variety of diagnostic purposes. In one aspect of the invention, an embodiment of the inventive apparatus 300 is applied to a patient's skin adjacent the synovial cavity of the patient's knee joint. The sample fluid thus obtained (e.g., interstitial fluid or capillary blood) is received by several sensors 340. Referring for example to FIG. 7, the sensors may include, inter alia, an impedance sensor 340a that is configured to detect IL-6; a photocell turbidity sensor 340b (which is disposed in registry with a light source of the reader module 306); a pH electrode 340c; an impedance sensor 340d that is configured to detect C-reactive protein; a viscosity sensor 340e; and a sensor 340f to differentiate gram(+) or gram(−) bacterial surface proteins. In addition, the sensor suite may include two or more electrodes for electrochemical detection of analytes, e.g., electrochemical immunoassay. Concurrently with obtaining the sample fluid, the optical detector 388 of the reader module 306 may scan the skin surface or the sample chamber 322 to detect a temperature of the skin or of the sample fluid, based on infrared light intensity.

Based on the sensor readings, the reader module 306 assesses for possible presence of synovial cavity infection. In particular, the microprocessor 376 compares readings from the sensors 340 to normal range values stored in the memory 374. In case one of the sensors 340 detects a higher than normal range concentration of IL-6, a lower than normal range pH, or a higher than normal range concentration of C-reactive protein, all of which are biomarkers of infection, then the reader module 306 generates a diagnostic alert to rule out synovial cavity infection. For example, the microprocessor 376 may cause a light emitting diode (LED) 394 to flash rapidly. Advantageously, this alerts a patient and care giver to an abnormal reading without requiring the delay associated with laboratory analysis and review of results. Additionally, in case one of the sensors 340 detects S. aureus specific antibodies (i.e. anti-staphylococcal IgG (immunoglobulin G) antibodies targeting two lipotechoic acid antigens), then the reader module 306 can generate a staphylococcus-specific diagnostic alert.

According to certain embodiments of the invention, the apparatus 300 can be single use or multiple use (with the same patient) for either discrete or continuous/real-time monitoring. Either way, for the patch deposition: the skin should be cleaned with chlorhexidine wipes prior to deposition and underneath packaging should be coating with antimicrobial hydrogel to insure no infection (sweat, etc.) and promote skin health/integrity (formulated with vitamin E, etc.) during the patch duration. For the multiple use, the microfluidic channels can be flushed, or sample fluid can be directed to separate sample chambers and sensing surfaces.

Other potential applications of the inventive apparatus include hydration and lactate monitoring for sports medicine, cancer diagnostic screening based on serum or plasma concentrations of cancer biomarkers, or continual glucose and glycated hemoglobin (HbAlc) sensing for diabetic patients.

Furthermore, in at least one embodiment of the present invention, the reader module 306 is placed in communication via the wireless communications package 386 with a cloud computing node 10 (e.g., a smart phone), as shown in FIG. 8. According to an exemplary embodiment of the present invention, the cloud computing node 10 is configured to transfer reader module data to the cloud environment 50, to facilitate diagnostic analysis of the reader module data by a cloud-hosted neural net, and/or to assess the reader module data using onboard heuristics. According to an exemplary embodiment of the present invention, the cloud computing node 10 is configured to display a diagnostic alert in case the reader module data matches an onboard heuristic or a neural net heuristic. The diagnostic alert includes, for example, a text message.

Thus, in some embodiments the cloud computing node (e.g., smart phone) 10 functions to receive data wirelessly from the reader module 306; store the received data; aggregate the data and undertake initial analysis with limited knowledge database; and thereby support in situ decision making. Further, in certain embodiments the cloud computing node 10 is configured to send a diagnostic alert to patient, care giver and physician based on local heuristics using the limited knowledge database. Such embodiments may reduce the importance and expense of the reader module 306 in the local diagnostic process. The cloud computing node 10 also is configured to send stored data into the cloud environment 50 for comprehensive cognitive analysis, to receive feedback from the cloud computing environment, and to execute one or more actions to implement that feedback. In certain embodiments, the cloud computing node 10 provides security of stored data, for example, through biometric verification of patient and attending care giver. In select embodiments, the smart phone 10 may also provide for wireless charging of the reader module battery 390.

Referring to the cloud computing environment 50, in certain embodiments this aspect of the invention provides for user administration, secure data storage, and an expert knowledge database. Leveraging the expert knowledge database, the cloud computing environment facilitates cognitive analytics to support decision making and execution based on the data received from the reader module 306. In certain embodiments, the cloud computing environment 50 is connected in secure wireless communication to the cloud computing node 10.

Figure 9:
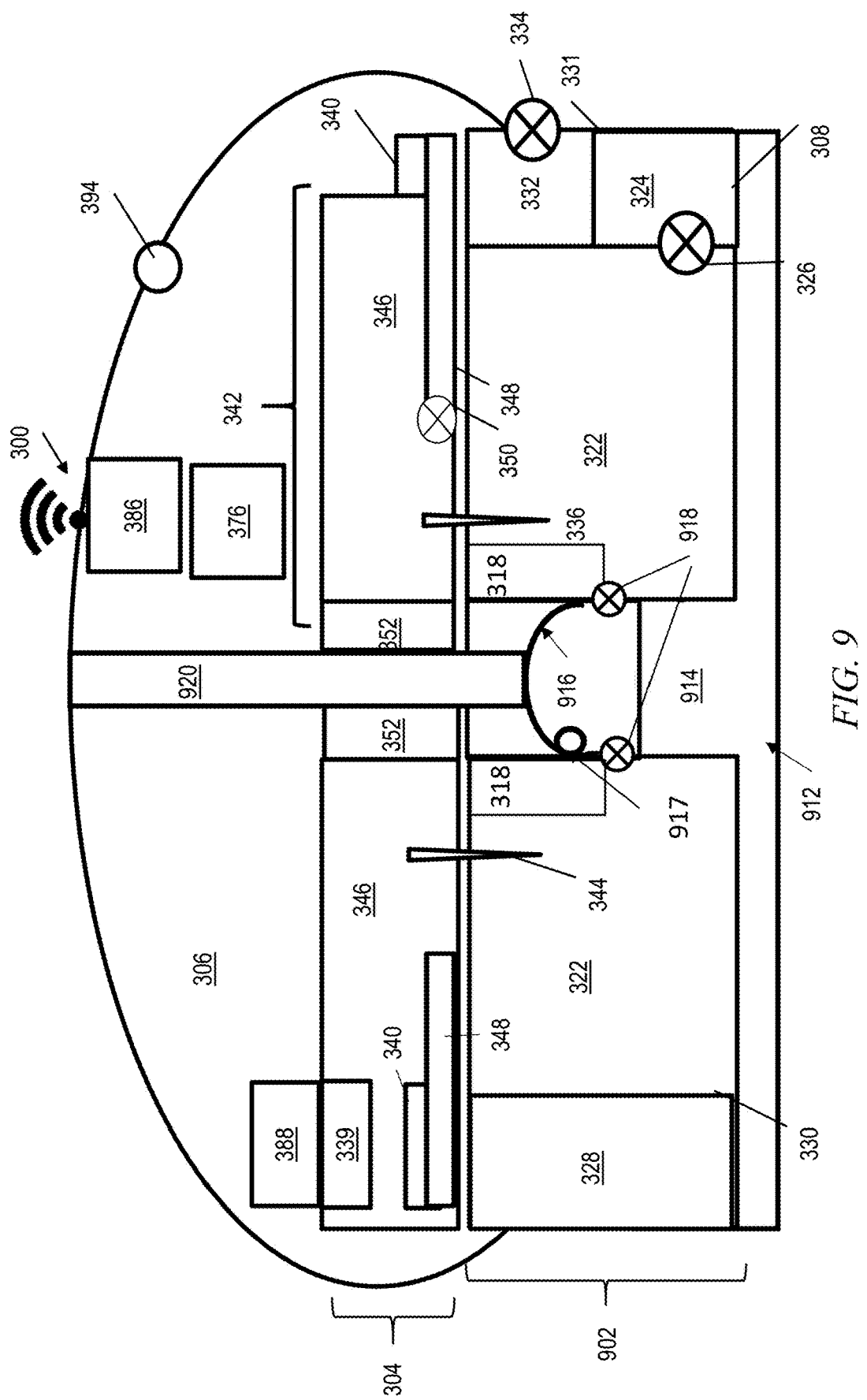
FIG. 9 depicts a sampling module usable in the apparatus of FIG. 3, according to another embodiment of the invention.

It will be appreciated by those of ordinary skill in the relevant art that various structural substitutions may be made without departing from the general concept of the invention. For example, referring to FIG. 9, all components alike to those of FIG. 3 are numbered alike. A sampling module 902 has sampling means 912 that includes a sponge 914 and a diaphragm pump 916. The diaphragm pump 916 includes an air vent 917. The diaphragm pump 916 is coupled in fluid communication with the sample chamber 322 via one way valves 918. The diaphragm pump 916 is operable by an actuator 920. In use of the sampling module 902, the sponge 914 will permit of absorbing skin surface fluid such as sweat. The sponge 914 may have either symmetric or asymmetric pore structures. Once the sponge 914 is saturated, the diaphragm pump 916 may be used to push fluid from the sponge 914 through the one way valves 918 into the sample chamber 322. Otherwise the sampling module 902 operates similarly to the sampling module 302.

Given the discussion thus far, and with reference to the drawing Figures, it will be appreciated that, in general terms, an exemplary aspect of the invention provides a microneedle diagnostic patch apparatus 300, which includes a sampling module 302 or 902 and an analysis module 304. The sampling module 302 or 902 includes sampling means for sampling fluid from a patient's skin when the sampling module is placed against the skin; for example, the sampling means 314 is a sampling microneedle, whereas the sampling means 912 includes a sampling sponge 914 and a diaphragm pump 916. The sampling module also includes a sample chamber 322 that is coupled in fluid communication with the sampling means. For example, the sample chamber 322 may be coupled in fluid communication with the sampling means 314 or 912 via a sample pump 318 and a blood cell filter 320. The sample pump 318 may be a solid-state pump, e.g., an electroosmotic pump or a weir-, trough-, or pillar-type capillary pump. The analysis module 304 includes a fluid conduit 342 that is coupled in fluid communication with the sample chamber 322 of the sampling module 302; and a plurality of sensors 340 that are coupled in fluid communication with the fluid conduit 342. For example, the fluid conduit 342 may include a capillary microchannel 348 that defines a sensor valve 350. In certain embodiments, the fluid conduit 342 may be coupled in fluid communication with an analyte pump 352, which may be a solid-state pump. At least one sensor of the plurality of sensors 340 may be an ion selective electrode, an impedance sensor, a viscosity sensor, a turbidity sensor, or an electrochemical assay sensor.

According to certain embodiments, the sampling module also may include at least one diluent chamber 328 containing an analytic diluent and coupled in fluid communication with the sample chamber via a diluent valve 330; and at least one reagent chamber 324 containing an anticoagulant reagent and coupled in fluid communication with the sample chamber via a reagent valve 326. At least one of the diluent valve or the reagent valve, if present, may be a solid-state valve. On the other hand, according to certain other embodiments, the sample chamber 322 may be pre-loaded with an analytic diluent and an anticoagulant reagent.

Certain embodiments of the inventive apparatus may also include a reader module 306, which has at least one optical sensor 388 coupled in optical communication with the sample chamber 322 of the sampling module 302; a microcontroller 376 coupled in electrical communication with the at least one sensor 340 of the analysis module; and a wireless communication package 386 coupled in electrical communication with the microcontroller.

In certain embodiments, the analysis module 304 may be disposed at a surface of the sampling module 302 opposite the at least one sampling microneedle 314. The reader module 306 may be disposed at a surface of the analysis module 304 opposite the sampling module 302. In such embodiments, the analysis module 304 has a window 339 in optical communication with the sample chamber 322 of the sampling module, and the optical sensor of the reader module is coupled in optical communication with the sample chamber via the window of the analysis module.

Other aspects of the invention provide a system, which includes a sampling module, an analysis module, a reader module, and a cloud computing node. The sampling module includes sampling means, such as a sampling sponge and diaphragm pump, or such as at least one sampling microneedle, for sampling fluid from a patient's skin when the sampling module is placed against the skin; and a sample chamber coupled in fluid communication with the sampling means. The analysis module includes a fluid conduit coupled in fluid communication with the sample chamber of the sampling module; and at least one sensor coupled in fluid communication with the fluid conduit. The reader module includes a microcontroller coupled in electrical communication with the at least one sensor of the analysis module; and a wireless communication package coupled in electrical communication with the microcontroller. The reader module also may include at least one optical sensor coupled in optical communication with the sample chamber of the sampling module. The cloud computing node is coupled in wireless communication with the wireless communication package of the reader module and is configured to transfer reader module data to a cloud environment. The cloud computing node may be further configured to facilitate diagnostic analysis of the reader module data by a cloud-hosted neural net; to assess the reader module data using onboard heuristics; and/or to display a diagnostic alert in case the reader module data matches an onboard heuristic or a cloud-hosted neural net heuristic.

Other aspects of the invention provide a computer program product, which includes a computer readable storage medium embodying computer executable instructions that when executed by a microprocessor cause the microprocessor to facilitate a method of actuating at least one of a sample pump or an analyte pump for sample fluid acquisition; actuating a sensor valve for sample fluid flow regulation; energizing one or more sensors for sample fluid analysis; receiving readings from the one or more sensors; comparing the sensor readings to a database of normal range values; and communicating with a cloud computing node.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

One or more embodiments of the invention, or elements thereof, can be implemented in the form of an apparatus including a memory and at least one processor that is coupled to the memory and operative to perform exemplary method steps. Such an apparatus will be described with particular reference to an embodiment of the invention, but variations will be apparent to the ordinary skilled worker.

One or more embodiments can make use of software running on a general purpose processor. With reference to FIG. 8, such an implementation might employ, for example, the microprocessor 376, the memory 374, and an input/output interface formed, for example, by the sensor interface(s) 368. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, mouse), and one or more mechanisms for providing results associated with the processing unit (for example, printer). The processor 376, memory 374, and input/output interface such as sensor interface(s) 368 can be interconnected, for example, via the system bus 392 within the reader module 306.

Accordingly, computer software including instructions or code for performing the methodologies of the invention, as described herein, may be stored in one or more of the associated memory devices 374 (for example, ROM, fixed or removable memory) and, when ready to be utilized, loaded in part or in whole (for example, into RAM) and implemented by the processor 376. Such software could include, but is not limited to, firmware, resident software, microcode, and the like.

A data processing system suitable for storing and/or executing program code could include at least the processor 376 coupled directly or indirectly to the memory elements 374 through the system bus 392. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards, displays, pointing devices, and the like) can be coupled to the system either directly (such as via the system bus) or through intervening I/O controllers (omitted for clarity).

Network adapters such as wireless communication package 386 may also be coupled to the system to enable the data processing system to become coupled to other data processing systems or remote printers or storage devices through intervening private or public networks. Modems, cable modem and Ethernet cards are just a few of the currently available types of network adapters.

As noted, aspects of the present invention may take the form of a computer program product embodied in one or more computer readable storage medium(s) having computer readable program code embodied thereon.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described.

One example of user interface that could be employed in some cases is hypertext markup language (HTML) code served out by a server or the like, to a browser of a computing device of a user. The HTML is parsed by the browser on the user's computing device to create a graphical user interface (GUI).

It should be noted that any of the methods described herein can include an additional step of providing a system comprising distinct software modules embodied on a computer readable storage medium; the modules can include, for example, any or all of the elements depicted in the block diagrams and/or described herein; by way of example and not limitation, a pump control module 378, a valve control module 380, and a sensor reading module 382. The method steps can then be carried out using the distinct software modules and/or sub-modules of the system, as described above, executing on one or more hardware processors 16. For example, the pump control module facilitates the step of actuating at least one of the sample pump 318 or the analyte pump 352 in response to the microneedles 314 being inserted through a patient's skin. Further, a computer program product can include a computer-readable storage medium with code adapted to be implemented to carry out one or more method steps described herein, including the provision of the system with the distinct software modules.

In any case, it should be understood that the components illustrated herein may be implemented in various forms of hardware, software, or combinations thereof; for example, application specific integrated circuit(s) (ASICS), functional circuitry, one or more appropriately programmed general purpose digital computers with associated memory, and the like. Given the teachings of the invention provided herein, one of ordinary skill in the related art will be able to contemplate other implementations of the components of the invention.

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++ or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A diagnostic patch apparatus comprising:
 a sampling module comprising:
  sampling means for sampling fluid from a patient's skin when the sampling module is placed against the skin;
  a sample chamber coupled in fluid communication with the sampling means;
  at least one diluent chamber containing an analytic diluent and coupled in fluid communication with the sample chamber via a diluent valve; and
  at least one reagent chamber containing an anticoagulant reagent and coupled in fluid communication with the sample chamber via a reagent valve; and an analysis module comprising:
  a fluid conduit coupled in fluid communication with the sample chamber of the sampling module; and
  a plurality of sensors coupled in fluid communication with the fluid conduit.

2. The apparatus of claim 1 wherein at least one of the diluent valve or the reagent valve is a solid-state valve.

3. The apparatus of claim 1 wherein the sample chamber of the sampling module is coupled in fluid communication with the sampling means via a blood cell filter and a sample pump.

4. The apparatus of claim 1 wherein the fluid conduit comprises a capillary microchannel that defines a sensor valve.

5. The apparatus of claim 1 wherein at least one sensor of the plurality of sensors is an ion selective electrode.

6. The apparatus of claim 1 wherein at least one sensor of the plurality of sensors is an impedance sensor.

7. The apparatus of claim 1 wherein at least one sensor of the plurality of sensors is a viscosity sensor.

8. The apparatus of claim 1 wherein the sampling means includes one of a microneedle or a sponge.

9. The diagnostic patch apparatus of claim 1 wherein the sampling means is a sampling microneedle positioned to penetrate the patient's skin when the sampling module is placed against the skin.

10. A diagnostic apparatus comprising:
a sampling module comprising:
   sampling means for sampling fluid from a patient's skin when the sampling module is placed against the skin; and
   a sample chamber coupled in fluid communication with the sampling means;
an analysis module disposed at a surface of the sampling module opposite the sampling means and comprising:
   a fluid conduit coupled in fluid communication with the sample chamber of the sampling module;
   a window overlying the sample chamber of the sampling module; and
   a plurality of sensors coupled in fluid communication with the fluid conduit; and
a reader module disposed at a surface of the analysis module opposite the sampling module and comprising:
   at least one optical sensor coupled in optical communication with the sample chamber of the sampling module, via the window of the analysis module;
   a microcontroller coupled in electrical communication with the at least one optical sensor and the plurality of sensors of the analysis module; and
   a wireless communication package coupled in electrical communication with the microcontroller.

11. A system comprising:
a sampling module comprising:
   sampling means for sampling fluid from a patient's skin when the sampling module is placed against the skin; and
   a sample chamber coupled in fluid communication with the sampling means;
an analysis module disposed at a surface of the sampling module opposite the sampling means and comprising:
   a fluid conduit coupled in fluid communication with the sample chamber of the sampling module;
   a window overlying the sample chamber of the sampling module; and
   a plurality of sensors coupled in fluid communication with the fluid conduit;
a reader module disposed at a surface of the analysis module opposite the sampling module and comprising:
   at least one optical sensor coupled in optical communication with the sample chamber of the sampling module, via the window of the analysis module;
   a microcontroller coupled in electrical communication with the at least one optical sensor and the plurality of sensors of the analysis module; and
   a wireless communication package coupled in electrical communication with the microcontroller; and
a cloud computing node coupled in wireless communication with the wireless communication package of the reader module and configured to transfer reader module data to a cloud environment.

12. The system of claim 11 wherein the cloud computing node is further configured to facilitate diagnostic analysis of the reader module data by a cloud-hosted neural net.

13. The system of claim 11 wherein the cloud computing node is further configured to assess the reader module data using onboard heuristics.

14. The system of claim 11 wherein the cloud computing node is configured to display a diagnostic alert in case the reader module data matches an onboard heuristic or a cloud-hosted neural net heuristic.

\* \* \* \* \*